(12) United States Patent
Lin

(10) Patent No.: US 7,135,021 B2
(45) Date of Patent: Nov. 14, 2006

(54) PLUG-TYPE DEVICE FOR RETRIEVING SPINAL COLUMN UNDER TREATMENT

(75) Inventor: Chih-I Lin, Taipei (TW)

(73) Assignees: A-Spine Holding Group Corp. (VG); A-Spine Asia Co., Ltd. (TW)

( * ) Notice: Subject to any disclaimer, the term of this patent is extended or adjusted under 35 U.S.C. 154(b) by 49 days.

(21) Appl. No.: 10/862,572

(22) Filed: Jun. 8, 2004

(65) Prior Publication Data
US 2005/0096654 A1 May 5, 2005

(30) Foreign Application Priority Data
Nov. 3, 2003 (TW) .............................. 92130635 A

(51) Int. Cl.
*A61B 17/56* (2006.01)
*A61B 17/58* (2006.01)

(52) U.S. Cl. ............................................ 606/61; 606/57
(58) Field of Classification Search ................... 606/61, 606/57
See application file for complete search history.

(56) References Cited
U.S. PATENT DOCUMENTS

| | | | |
|---|---|---|---|
| 6,749,613 B1 * | 6/2004 | Conchy et al. ............... | 606/61 |
| 2002/0173791 A1 * | 11/2002 | Howland ...................... | 606/61 |
| 2006/0036252 A1 * | 2/2006 | Baynham et al. ............. | 606/73 |
| 2006/0058787 A1 * | 3/2006 | David .......................... | 606/61 |

* cited by examiner

*Primary Examiner*—Alvin J. Stewart
(74) *Attorney, Agent, or Firm*—Bacon & Thomas PLLC

(57) ABSTRACT

A plug-type spinal retrieving device includes a retrieval rod; a fastening screw assembly including a fastening screw and a C-shaped ring having a convex outer surface; a plug; and a fixation seat having a receiving hole in which the retrieval rod is slidably received, a fastening hole having a concave wall in which the C-shaped ring is rotatably received, and an interconnecting hole through which the receiving hole communicates with the fastening hole. The C-shaped ring is mounted on the fastening screw, so that the fastening screw is grasped by the C-shaped ring, when the C-shaped ring is received in the fastening hole of the fixation seat. The C-shaped ring and the retrieval rod are immobilized in the fastening hole and the receiving hole of the fixation seat by inserting the plug into the interconnecting hole.

2 Claims, 3 Drawing Sheets ic # PLUG-TYPE DEVICE FOR RETRIEVING SPINAL COLUMN UNDER TREATMENT

FIELD OF THE INVENTION

The present invention relates generally to a spinal surgical care device, and more particularly to a rotary device for retrieving spine column under treatment.

BACKGROUND OF THE INVENTION

The conventional spinal retrieval devices use complicated locking mechanisms to secure a rod with a spinal screw or hook body such as those disclosed in U.S. Pat. Nos. 5,147,359 and 6,602,253. Consequently, the conventional spinal retrieval devices complicate the spinal surgery and prolong the surgery time.

SUMMARY OF THE INVENTION

A primary objective of the present invention is to provide a rotary device for fixing spinal column under treatment without the drawbacks of the prior art.

A plug-type spinal retrieving device constructed according to the present invention comprises:

a retrieval rod;

a fastening screw assembly comprising a fastening screw and a C-shaped ring having a convex outer surface;

a plug; and a fixation seat having a receiving hole in which the retrieval rod is able to be slidably received, a fastening hole having a concave wall in which the C-shaped ring is able to be rotatably received, and an interconnecting hole through which the receiving hole communicates with the fastening hole; wherein the fastening screw has a threaded portion and an upper portion, and the C-shaped ring is mounted on the upper portion of the fastening screw, so that the fastening screw is grasped by the C-shaped ring, when the C-shaped ring is received in the fastening hole of the fixation seat; and the C-shaped ring and the retrieval rod are immobilized in the fastening hole and the receiving hole of the fixation seat by inserting the plug into the interconnecting hole of the fixation seat, when the retrieval rod is received in the receiving hole, and the C-shaped ring mounted on the fixation screw is received in the fastening hole of the fixation seat.

Preferably, the C-shaped ring has a slot.

Preferably, the interconnecting hole has a longitudinal axis parallel to a longitudinal axis of the fastening hole. More preferably, the plug has a tapered end with two slant surfaces, on which a round recess and a groove are formed separately, wherein the round recess has a dimension corresponding to the convex outer surface of the C-shaped ring, and the groove has a dimension corresponding to the retrieval rod.

Preferably, the fastening hole has a longitudinal axis parallel to a longitudinal axis of the interconnecting hole. More preferably, the plug has two arcuate claws at one side and a round recess on a slant surface at another side thereof, wherein the arcuate claws and the receiving hole together form a mechanism for grasping the retrieval rod in the receiving hole, and the round recess on the slant surface increases the contact area between the plug and the C-shaped ring.

The plug-type spinal retrieving device of the present invention has no threaded studs for locking the retrieval rod with the fastening screw, and uses a plug instead, so that the operation is relatively easier, and thus a shorter operation time is required. Further, thanks to the convex outer surface of the C-shaped ring and the corresponding concave wall of the fastening hole, the coupling of the retrieval rod with the fastening screw can be easily adjusted before the plug is inserted in place.

The features and the advantages of the present invention will be more readily understood upon a thoughtful deliberation of the following detailed description of the present invention with reference to the accompanying drawings.

DETAILED DESCRIPTION OF THE PREFERRED EMBODIMENT

Figure 1:
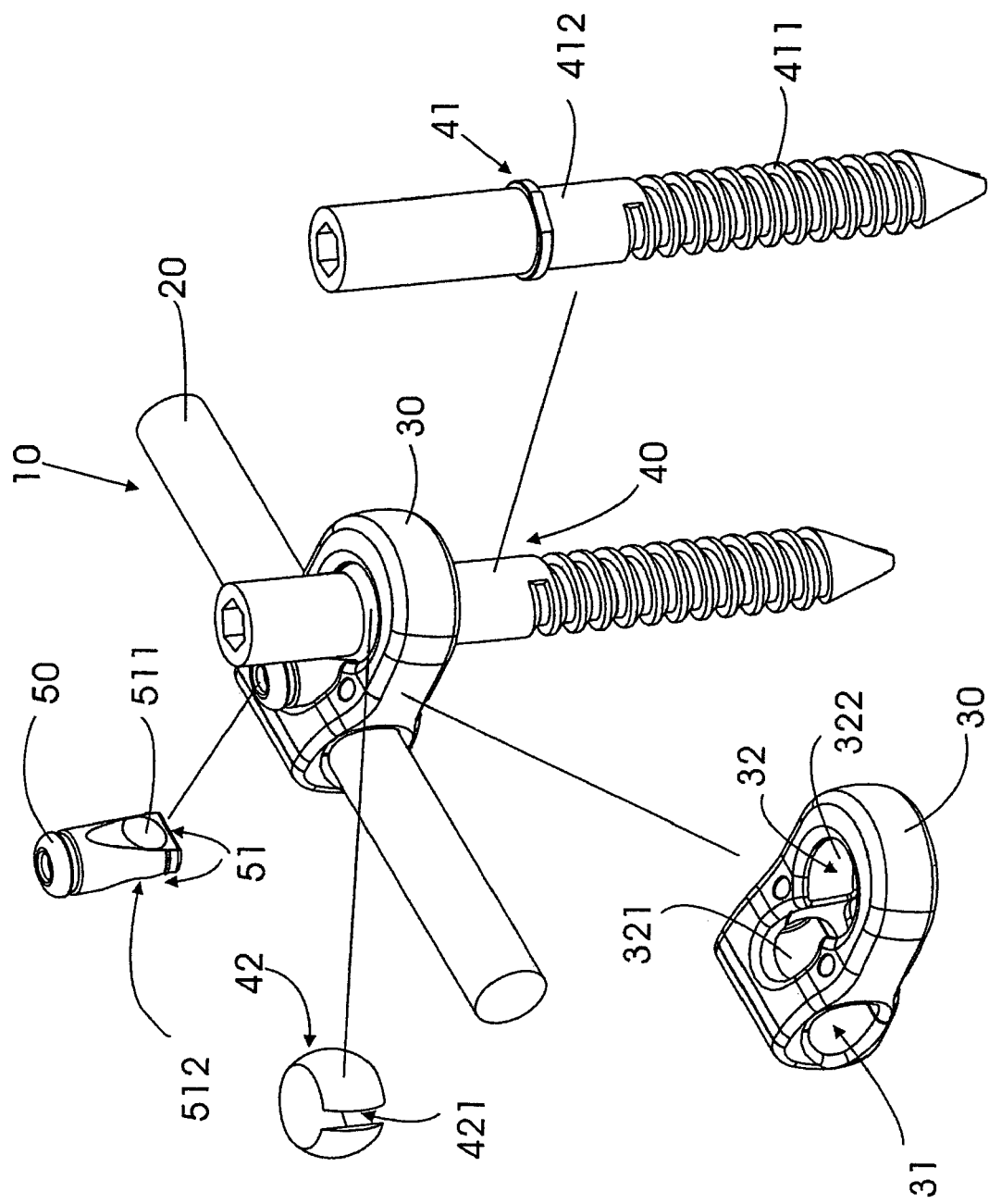
FIG. 1 shows an exploded perspective view of a first preferred embodiment of the present invention.

A plug-type spinal retrieving device 10 constructed according to one of the preferred embodiments of the present invention is shown in FIG. 1, which includes a retrieval rod 20; a fastening screw assembly 40 including a fastening screw 41 and a C-shaped ring 42; a plug 50; and a fixation seat 30 having a receiving hole 31 in which the retrieval rod 20 is slidably received, a fastening hole 32 having a concave wall 322 in which the C-shaped ring 42 is rotatably received, and an interconnecting hole 321 through which the receiving hole 31 communicates with the fastening hole 32.

The fastening screw 41 has a threaded portion 411 and an upper portion with a flange between the two portions. The C-shaped ring 42 is put on the upper portion and retained by the flange of the fastening screw 41. The C-shaped ring 42 has a slot 421 and a convex outer surface corresponding to the concave wall 322 of the fastening hole 32, so that the C-shaped ring 42 can be compressed and rotatably received in the fastening hole 32, while the fastening screw 41 is grasped by the C-shaped ring 42 in the fastening hole 32 of the fixation seat 30. The fastening screw 41 together with the fixation seat 30 is then threaded into a pedicle of a vertebra (not shown in the drawing) by using a tool hole on the top of the fastening screw 41. The retrieval rod 20 is inserted into the receiving hole 31 and then the angle and the direction of the fixation seat 30 relative to the fastening screw 41 are adjusted.

The plug 50 has a tapered end with two slant surfaces 51, on which a round recess 511 and a groove 512 are formed separately. The round recess 511 has a dimension corresponding to the convex outer surface of the C-shaped ring 42, and the groove 512 has a dimension corresponding to the retrieval rod 20, so that the C-shaped ring 42 and the retrieval rod 20 are immobilized by pressing after the plug 50 is inserted into the interconnection hole 321.

Figure 2A:
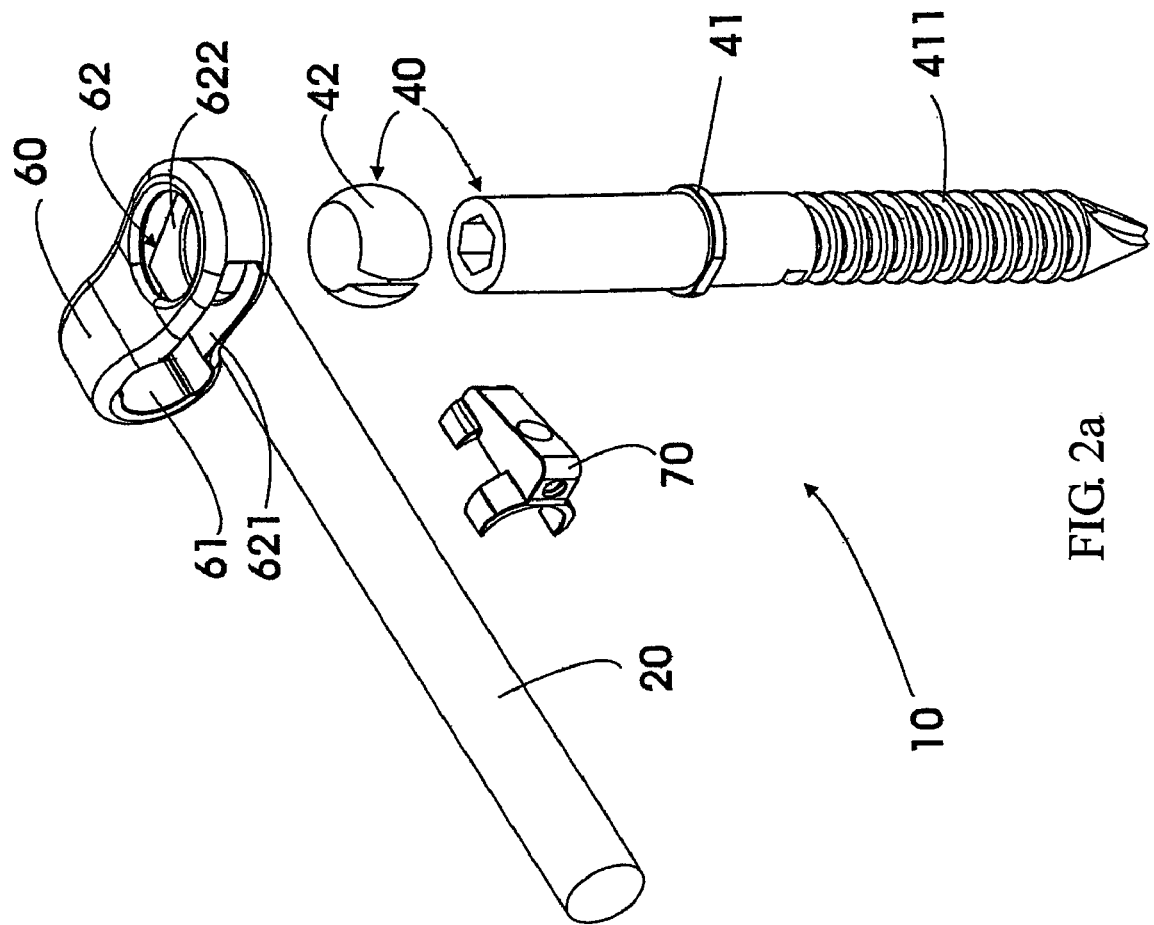
FIG. 2*a* shows an exploded perspective view of a second preferred embodiment of the present invention.
Figure 2B:
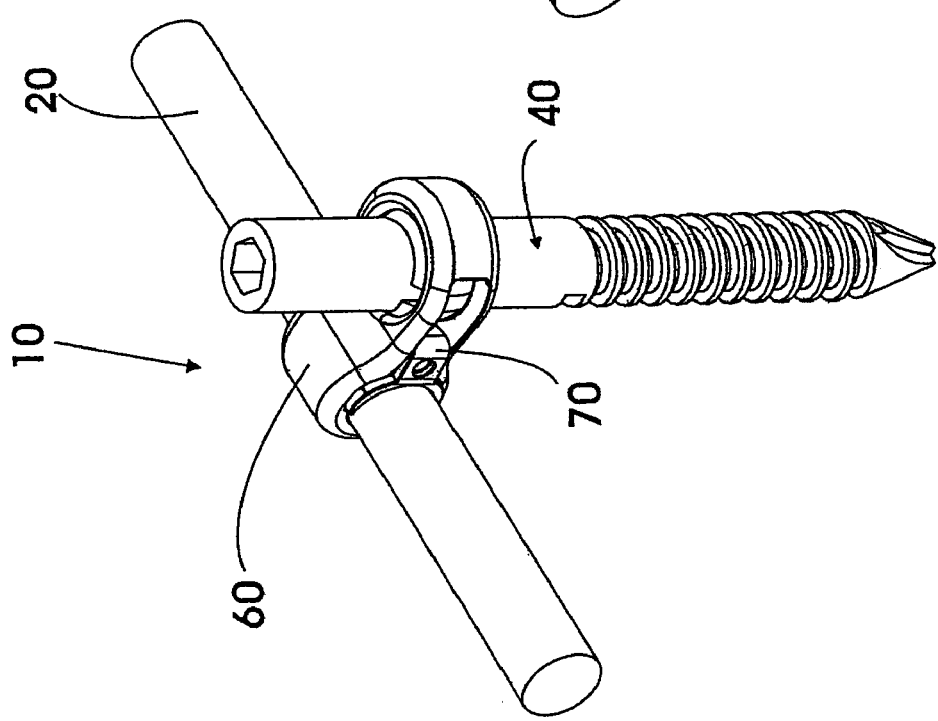
FIG. 2*b* shows a perspective view of the second preferred embodiment of the present invention shown in FIG. 1 at work.
Figure 3:
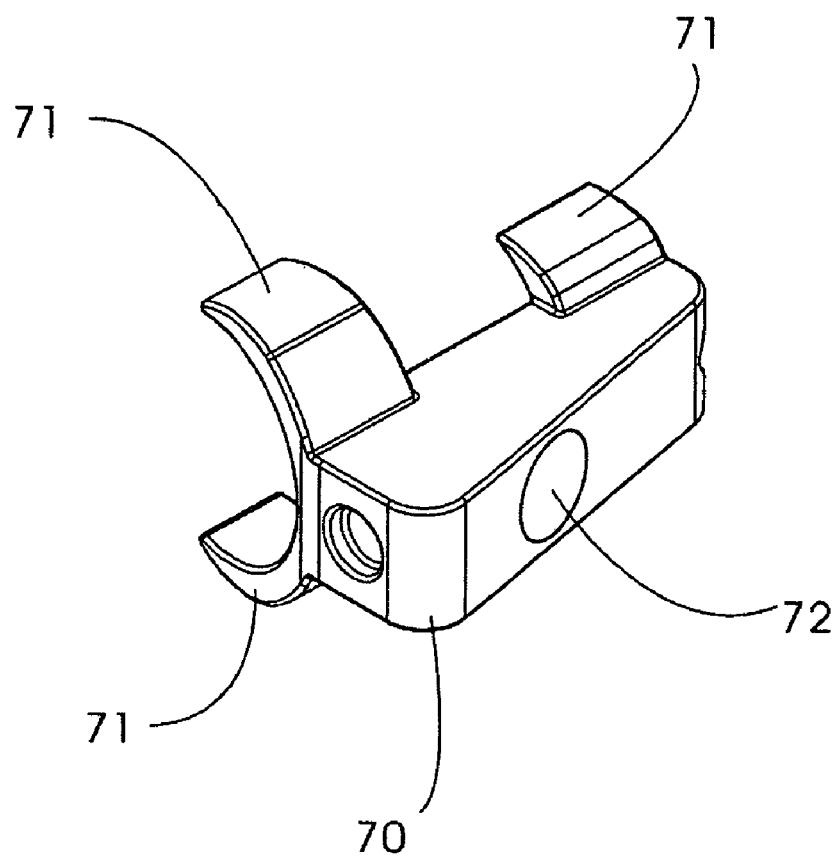
FIG. 3 shows a perspective view and a top plan view of the plug 70 used in the second preferred embodiment of the present invention shown in FIGS. 2*a* and 2*b*.
Figure 3:
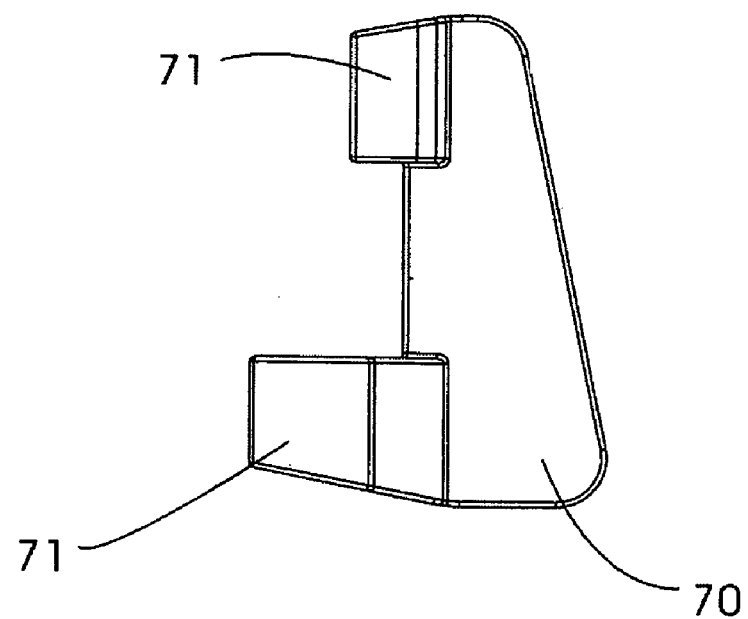

Another preferred embodiment of the plug-type spinal retrieving device 10 of the present invention similar to the first embodiment shown in FIG. 1 but having a different fixation seat 60 and a different plug 70 is shown in FIGS. 2*a*, 2b and 3, in which like elements are represented by like numerals. In this embodiment, the fixation seat 60 is provided with an interconnecting hole 621 at a lateral side thereof, through which a receiving hole 61 communicates with a fastening hole 62 having a concave wall 622. The fastening screw assembly 40 (the fastening screw 41 and the C-shaped ring 42) and the retrieval rod 20 are mounted to the fixation seat 60 the same way as in the first embodiment shown in FIG. 1. The plug 70 has two arcuate claws 71 at one side and a round recess 72 on a slant surface at another side thereof, and is inserted into the interconnecting hole 621 to fasten the C-shaped ring 42 and the retrieval rod 20 in the fixation seat 60 at the same time. The arcuate claws 71 and the receiving hole 61 together form a mechanism for grasping the retrieval rod 20 in the receiving hole 61. The slant surface of the plug 70 helps its insertion between the retrieval rod 20 and the C-shaped ring 42, and the round recess 72 thereon increases the contact area between the plug 70 and the C-shaped ring 42, so that the fixation of the C-shaped ring in the fastening hole 622 is enhanced.

What is claimed is:

1. A plug-type spinal retrieving device comprising:
   a retrieval rod;
   a fastening screw assembly comprising a fastening screw and a C-shaped ring having a convex outer surface;
   a plug having a tapered end with two slant surfaces, on which a round recess and a groove are formed separately, wherein the round recess has a dimension corresponding to the convex outer surface of the C-shaped ring, and the groove has a dimension corresponding to the retrieval rod; and
   a fixation seat having a receiving hole in which the retrieval rod is able to be slidably received, a fastening hole having a concave wall in which the C-shaped ring is able to be rotatably received, and an interconnecting hole through which the receiving hole communicates with the fastening hole, the interconnecting hole having a longitudinal axis parallel to a longitudinal axis of the fastening hole; wherein
   the fastening screw has a threaded portion and an upper portion, and the C-shaped ring is mounted on the upper portion of the fastening screw, so that the fastening screw is grasped by the C-shaped ring, when the C-shaped ring is received in the fastening hole of the fixation seat; and
   the C-shaped ring and the retrieval rod are immobilized in the fastening hole and the receiving hole of the fixation seat by inserting the plug into the interconnecting hole of the fixation seat, when the retrieval rod is received in the receiving hole, and the C-shaped ring mounted on the fixation screw is received in the fastening hole of the fixation seat.

2. The device according to claim 1, wherein the C-shaped ring has a slot.

* * * * *